(12) United States Patent
Muratayev et al.

(10) Patent No.: US 7,801,586 B2
(45) Date of Patent: Sep. 21, 2010

(54) ANTENNA FOR IN-VIVO IMAGING SYSTEM

(75) Inventors: Alex Muratayev, Yoqneam (IL); Ido Bettesh, Haifa (IL); Semion Khait, Tiberias (IL)

(73) Assignee: Given Imaging Ltd., Yoqneam Ilite (IL)

( * ) Notice: Subject to any disclaimer, the term of this patent is extended or adjusted under 35 U.S.C. 154(b) by 1000 days.

(21) Appl. No.: 11/268,463

(22) Filed: Nov. 8, 2005

(65) Prior Publication Data
US 2006/0241422 A1 Oct. 26, 2006

(30) Foreign Application Priority Data
Mar. 31, 2005 (IL) .................................... 167782

(51) Int. Cl.
A61B 5/05 (2006.01)
A61B 1/06 (2006.01)
A61B 1/04 (2006.01)
A61B 5/00 (2006.01)
A61B 6/00 (2006.01)
H01P 11/00 (2006.01)

(52) U.S. Cl. .................. 600/407; 600/160; 600/109; 600/476; 600/300; 29/600

(58) Field of Classification Search ............. 600/407, 600/160, 109, 300, 476; 29/600
See application file for complete search history.

(56) References Cited

U.S. PATENT DOCUMENTS

| 3,218,638 | A | * | 11/1965 | Honig | ................ | 342/50 |
|---|---|---|---|---|---|---|
| 3,509,270 | A | | 4/1970 | Dube et al. | | |
| 3,616,532 | A | | 11/1971 | Beck | | |
| 3,683,389 | A | | 8/1972 | Hollis | | |
| 3,971,362 | A | | 7/1976 | Pope et al. | | |
| 4,278,077 | A | | 7/1981 | Mizumoto | | |
| 4,689,621 | A | | 8/1987 | Kleinberg | | |
| 4,741,327 | A | | 5/1988 | Yabe | | |
| 4,742,817 | A | | 5/1988 | Kawashima et al. | | |
| 4,844,076 | A | | 7/1989 | Lesho et al. | | |
| 4,860,732 | A | | 8/1989 | Hasegawa et al. | | |
| 5,279,607 | A | | 1/1994 | Schentag et al. | | |
| 5,398,689 | A | | 3/1995 | Connor et al. | | |
| 5,426,263 | A | | 6/1995 | Potter et al. | | |

(Continued)

FOREIGN PATENT DOCUMENTS

DE 3440177 5/1976

(Continued)

OTHER PUBLICATIONS

English translation of JP 2001-091860 provided by IPDL tool.*

(Continued)

Primary Examiner—Eric F Winakur
Assistant Examiner—Katherine L Fernandez
(74) Attorney, Agent, or Firm—Pearl Cohen Zedek Latzer, LLP

(57) ABSTRACT

The invention provides a device, and method for in vivo imaging, for example, using an in vivo imaging device including a circuit board having rigid sections and flexible sections. The circuit board may include one or more layers and an antenna may be embedded into one or more layers.

11 Claims, 17 Drawing Sheets

U.S. PATENT DOCUMENTS

| | | | |
|---|---|---|---|
| 5,448,511 A | 9/1995 | Paurus et al. | |
| 5,454,366 A | 10/1995 | Ito et al. | |
| 5,604,531 A | 2/1997 | Iddan et al. | |
| 5,679,216 A | 10/1997 | Takayama et al. | |
| 5,725,474 A | 3/1998 | Yasui et al. | |
| 5,754,313 A | 5/1998 | Pelchy et al. | |
| 5,807,266 A | 9/1998 | Itonaga et al. | |
| 5,819,736 A | 10/1998 | Avny et al. | |
| 5,833,603 A | 11/1998 | Kovacs et al. | |
| 5,929,901 A | 7/1999 | Adair et al. | |
| 5,986,693 A | 11/1999 | Adair et al. | |
| 5,993,378 A | 11/1999 | Lemelson | |
| 6,043,839 A | 3/2000 | Adair et al. | |
| 6,240,312 B1 | 5/2001 | Alfano et al. | |
| 6,313,456 B1 | 11/2001 | Miyashita et al. | |
| 6,338,347 B1 | 1/2002 | Chung | |
| 6,371,927 B1 | 4/2002 | Brune et al. | |
| 6,417,885 B1 | 7/2002 | Suzuki et al. | |
| 6,632,175 B1 | 10/2003 | Marshall | |
| 6,709,387 B1 | 3/2004 | Glukhovsky et al. | |
| 2001/0006252 A1 | 7/2001 | Kim et al. | |
| 2001/0017649 A1 | 8/2001 | Yaron | |
| 2001/0051766 A1 | 12/2001 | Gazdzinski | |
| 2002/0103417 A1 | 8/2002 | Gazdzinski | |
| 2002/0198439 A1 | 12/2002 | Mizuno | |
| 2003/0028078 A1 | 2/2003 | Glukhovsky | |
| 2003/0043263 A1 | 3/2003 | Glukhovsky et al. | |
| 2003/0114742 A1 | 6/2003 | Lewkowicz et al. | |
| 2003/0117491 A1 | 6/2003 | Avni et al. | |
| 2003/0171648 A1 | 9/2003 | Yokoi et al. | |
| 2003/0171649 A1 | 9/2003 | Yokoi et al. | |
| 2003/0171652 A1 | 9/2003 | Yokoi et al. | |
| 2004/0027459 A1 | 2/2004 | Segawa et al. | |
| 2004/0087832 A1 | 5/2004 | Glukhovsky et al. | |
| 2004/0171914 A1* | 9/2004 | Avni | 600/160 |
| 2006/0004257 A1* | 1/2006 | Gilad et al. | 600/160 |

FOREIGN PATENT DOCUMENTS

| | | |
|---|---|---|
| EP | 1 104 182 | 5/2001 |
| JP | 57-45833 | 3/1982 |
| JP | 3-289779 | 12/1991 |
| JP | 4109927 | 4/1992 |
| JP | 4-180736 | 6/1992 |
| JP | 5015515 | 1/1993 |
| JP | 7289504 | 11/1995 |
| JP | 9238900 | 9/1997 |
| JP | 2001091860 | 4/2001 |
| JP | 2001095755 | 4/2001 |
| JP | 2001095756 | 4/2001 |
| JP | 2001104241 | 4/2001 |
| JP | 2001104242 | 4/2001 |
| JP | 2001104243 | 4/2001 |
| JP | 2001104244 | 4/2001 |
| JP | 2001104287 | 4/2001 |
| JP | 2001137182 | 5/2001 |
| JP | 2001224551 | 8/2001 |
| JP | 2001224553 | 8/2001 |
| WO | WO 92-21307 | 12/1992 |
| WO | WO 98/11816 | 3/1998 |
| WO | WO 00-22975 | 4/2000 |
| WO | WO 01/08548 | 2/2001 |
| WO | WO 01/50941 | 7/2001 |
| WO | WO 01/65995 | 9/2001 |
| WO | WO 02-067593 | 8/2002 |
| WO | WO 02-094337 | 11/2002 |
| WO | WO 02-095351 | 11/2002 |
| WO | WO 03-003706 | 1/2003 |
| WO | WO 03-011103 | 2/2003 |
| WO | WO 2004-028335 | 4/2004 |
| WO | WO2004/028336 | 4/2004 |

OTHER PUBLICATIONS

U.S. Appl. No. 10/493,751, filed Apr. 27, 2004, Glukhovsky et al.
BBC News Online—"Pill camera to 'broadcast from the gut'", Feb. 21, 2000, www.news.bbc.co.uk.
international Search Report of PCT/IL02/00480 dated Sep. 17, 2003.
International Search Report dated May 19, 2006 from Application No. PCT/IL2005/001380.
Office Communication U.S. Appl. No. 10/879,054 Date Mailed: Nov. 17, 2005.
Robots for the Future—Shin-ichi, et al., Nov. 29, 2001.
"The Radio Pill", Rowlands, et al., British Communications and Electronics, Aug. 1960, pp. 598-601.
"Video Camera to Take"—RF System lab, Dec. 25, 2001.
Wang, et al., "Integrated Micro-Instrumentation for Dynamic Monitoring of the Gastro-Intestinal Tract", Presented at IEEE Instrumentation and Measurement Technology Conference, May 2002, Anchorage, Ak, USA, www.see.ed.ac.uk/Naa.publications.html.
"Wellesley company sends body montiors into space"—Crum, Apr. 1998.
"Wireless transmission of a color television movino image from the stomach using a miniature CCD camera. light source and microwave transmitter". Swain CP, Gong F, Mills TN. Gastrointest Endosc 1997;45:AB40.
www.rfnorkia.com—NORIKA3, Dec. 24, 2001.

* cited by examiner

ANTENNA FOR IN-VIVO IMAGING SYSTEM

CROSS-REFERENCE TO RELATED APPLICATIONS

The present application claims priority from Israeli Patent Application IL 167782, filed 31 Mar. 2005, which is hereby incorporated by reference in its entirety.

FIELD OF THE INVENTION

The present invention relates generally to an in-vivo imaging system suitable for imaging the gastrointestinal (GI) tract or other body lumens. In particular, it is related to an imaging device and an antenna for transmitting for example captured image signals.

BACKGROUND OF THE INVENTION

Known devices may be helpful in providing in-vivo imaging. Autonomous in-vivo imaging devices, for example in-vivo imaging devices, such as swallowable or ingestible capsules or other devices may move through a body lumen, imaging as they move along. Some of these devices use a wireless connection to transmit image data.

In some in vivo devices, such as ingestible imaging capsules, the components within the capsule, such as an antenna (s), may be arranged on a board or on several boards, for example on a printed circuit board (PCB). In some cases the boards are aligned along an axis of the capsule and are electrically connected by one or more wires.

The efficiency of an antenna is in general determined by characteristics of the antenna among which are the surface area and/or the size of the antenna. For example, as long an antenna is significantly smaller than its transmission wave length, the reception and transmission efficiency of an antenna increases in direct relation to the surface area and/or the length of the antenna e.g. the longer the antenna is and/or the bigger the surface area of the antenna is, the more efficient it is.

Several factors have so far limited the extent to which the size of an antenna can be increased. One of the factors may be the size of the imaging device.

SUMMARY OF THE INVENTION

The present invention provides, according to some embodiments, an in vivo imaging device comprising a circuit board, for example a flexible circuit board and/or a circuit board having one or more rigid sections or portions, and one or more flexible sections or portions. In some embodiments, the rigid sections and flexible sections may alternate.

According to one embodiment of the present invention, an example for economizing space usage may be by employing rigid and/or flexible sections as a support for several components. For example, according to one embodiment of the present invention a rigid section may support both an illumination system and/or an antenna, and thus decrease the number of rigid and flexible sections on the circuit board. Efficient and economized circuit board setup may enable circuit board folding into smaller sizes which take up less space, and thus may provide for smaller sized in-vivo devices or for more usable space within an in vivo device.

According to some embodiments of the present invention, the in vivo imaging device may include an image sensor. The device may further include an illumination system and a transmitter and an antenna for transmitting image data to a receiving system. According to one embodiment the transmitter is a wireless transmitter.

According to some embodiments of the present invention one or more rigid portions may include an illumination system or one or more illumination units, for example a Light Emitting Diodes (LEDs), a LED ring, an illumination ring, an illumination assembly, or other suitable illumination systems on a first surface of the rigid portion and an antenna on a second surface of the rigid portion.

According to some embodiments of the present invention, one or more illumination units, for example a LED ring or other suitable illumination system and the antenna may be integrated or embedded, for example, within a rigid portion and/or the flexible portion of the circuit board. According to some embodiments of the present invention the antenna may be combined with or attached to other elements in the in vivo imaging device so as to possibly reduce the amount of space taken up by it.

According to some embodiments of the present invention there is provided an imaging device wherein a transmitter may include a Matching Component and/or a voltage-controlled oscillator (VCO), and an antenna may be a resonating loop of the VCO.

According to some embodiments of the present invention there is provided an imaging device which may include an antenna which has conductors in three dimensions; a three dimensional (3D) antenna. According to some embodiments of the present invention the 3D antenna may be embedded alongside or in a circuit board.

According to some embodiments of the present invention there is provided an antenna which may include one or more substances such as a ferrite, for improving the efficiency of the antenna.

According to some embodiments of the present invention there is provided an imaging device having a shell or housing, and wherein an antenna may be disposed on the shell or housing.

According to another embodiment of the present invention, the antenna may be disposed along a perimeter of the inner side of shell or housing, and the perimeter may lie in a plane parallel to a short axis of the housing; in a plane forming a non-perpendicular angle with a long axis of the housing; or in a plane parallel to a long axis of the housing, or wherein the antenna may be disposed along a perimeter of the outer side of the shell or housing.

BRIEF DESCRIPTION OF THE DRAWINGS

The invention is herein described, by way of example only, with reference to the accompanying drawings, in which like components are designated by like reference numerals, wherein.

Figure 1:
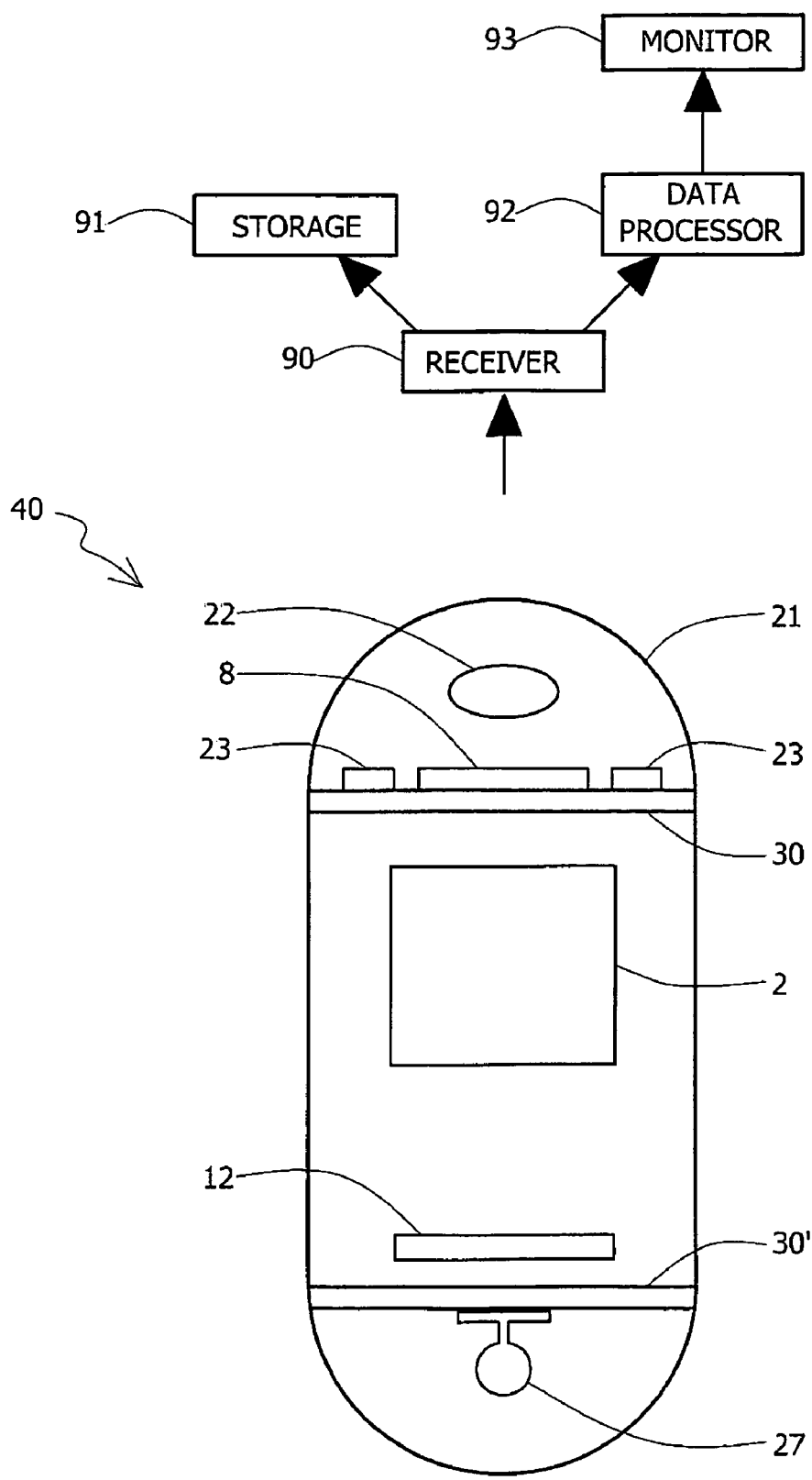
FIG. 1 shows a schematic diagram of an in vivo imaging device and system, according to one embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the following detailed description, numerous specific details are set forth in order to provide a thorough understanding of the present invention. However, it will be understood by those skilled in the art that the present invention may be practiced without these specific details. In other instances, well-known methods, procedures, and components have not been described in detail so as not to obscure the present invention.

Reference is now made to FIG. 1, which schematically illustrates an in vivo imaging device according to an embodiment of the present invention. According to one embodiment, the device 40 typically comprises an optical window 21 and an imaging system for obtaining images from inside a body lumen, such as the GI tract. The imaging system may include one or more illumination sources 23, such as a white LED and/or OLEDs (Organic LED), an imager 8, such as a CMOS and/or a CCD imaging camera and an optical system 22 which focuses the images onto the imager 8. The illumination source 23 illuminates the inner portions of the body lumen through optical window 21. According to the embodiments of the invention as will be described below, device 40 may include a transmitter 12 and/or a receiver and an antenna 27, for transmitting image signals, typically for wirelessly transmitting signals from the imager 8, and a power source 2, such as a silver oxide battery, that provides power to the electrical elements of the device 40. According to one embodiment the transmitter 12 is an RF transmitter. Other wireless transmitters can be used. According to one embodiment, device 40 may include one or more supports, such as two different PCBs 30 and 30', or a single PCB which may include two parts. According to one embodiment of the present invention, the various components of the device 40, such as the transmitter 12, the antenna 27 and the imager 8 may be disposed on a support, for example the PCB 30 According to some embodiments of the present invention, outside a patient's body may be, for example, an image receiver 90 (including, for example, an antenna or an antenna array), a storage unit 91, a data processor 92, and a monitor 93.

According to some embodiments of the present invention, device 40 may communicate with an external receiving and display system (e.g., through receiver 90) to provide display of data, control, or other functions. For example, power may be provided to device 40 using an internal battery, an internal power source, or a wireless system to receive power. Other embodiments may have other configurations and capabilities. For example, components may be distributed over multiple sites or units, and control information may be received from an external source e.g. through a control channel.

According to some embodiments of the present invention, device 40 typically may be or may include, for example, an autonomous swallowable capsule, but device 40 may have other shapes and need not be swallowable or autonomous. Embodiments of device 40 are typically autonomous, and are typically self-contained. For example, device 40 may be a capsule or other unit where all the components are substantially contained within a container shell or housing, and where device 40 does not require any wires or cables to, for example, receive power or transmit information.

According to some embodiments of the present invention, the device 40 may be capsule shaped and can operate as an autonomous endoscope for imaging the GI tract. However, other devices, such as devices designed to be incorporated in an endoscope, catheter, stent, needle, etc., may also be used, according to embodiments of the invention. Furthermore, the device 40 need not include all the elements described above. For example, the device 40 need not include an internal light source or an internal power source; illumination and/or power may be provided from an external source, as known in the art.

The system and method of the present invention may be used with or in an imaging system such as that described in U.S. patent application Ser. No. 09/800,470, entitled A DEVICE AND SYSTEM FOR IN-VIVO IMAGING, filed on Mar. 8, 2001. A further example of an imaging system with which the system and method of the present invention may be used is described in U.S. Pat. No. 5,604,531 to Iddan et al., entitled IN-VIVO VIDEO CAMARA SYSTEM, filed on Jan. 17, 1995. Both these publications are assigned to the common assignee of the present application and are hereby incorporated by reference. Alternatively, the system of the present invention may be utilized in any suitable imaging device providing images of a body lumen or cavity. For example, a circuit board according to an embodiment of the invention may be utilized in probes used for in vivo imaging, such as endoscopes.

Figure 2:
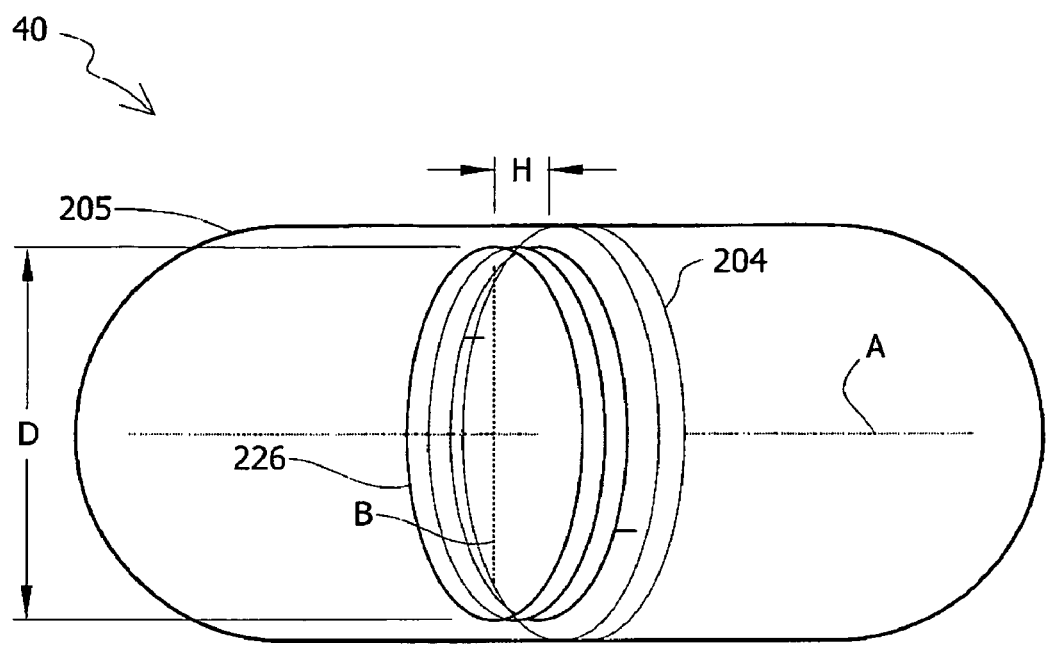
FIG. 2 is a schematic illustration of an antenna, inside a shell of an imaging device, in accordance with some embodiments of the present invention.

FIG. 2 is a schematic illustration of a vertical antenna 226 comprising a vertically oriented air coil, according to some embodiments of the present invention. When used herein, vertical and horizontal are relative terms, and may be interchangeable based on perspectives of the viewer, or based on specific embodiments. In one embodiment, antenna 226 may be included within an in-vivo device 40, having a shell or housing 205, and antenna 226 may be oriented so that it circles along (and perpendicularly to) axis "A" of the housing 205 of device 40 and extends vertically more or less along axis B. In other words, a plane formed by the loop(s) or coil(s) of antenna 226 may be relatively perpendicular to axis A, or may be oriented relatively horizontally and parallel to the plane of a supporting board 204, e.g., a print-circuit-board (PCB) or other holders. While in one embodiment the loop(s) or coil(s) may be substantially circular, in other embodiments they may have other shapes, such as an oval, a square, etc.

Figure 3:
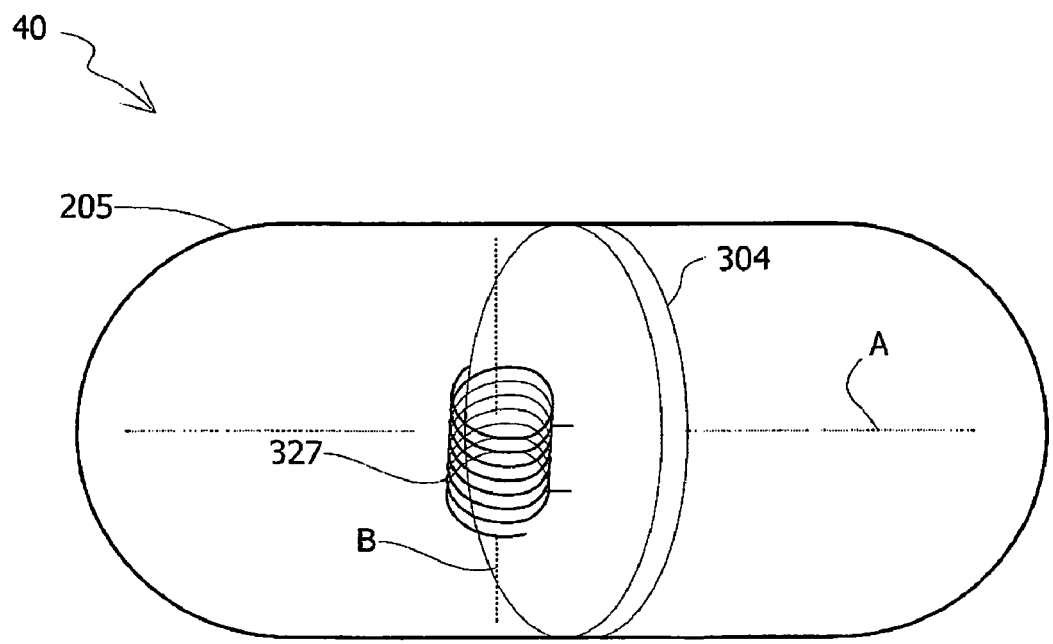
FIG. 3 is a schematic illustration of an antenna, inside a shell of an imaging device, comprising a horizontally oriented air coil, in accordance with some embodiments of the present invention.

According to some embodiments of the present invention, the PCB 204 and loops formed by antenna 226 may be oriented in a plane parallel to or substantially parallel to a short axis "B" of the housing 205 of device 40, and/or may be perpendicular to or substantially perpendicular to long axis A. Deviations from "horizontal" and "vertical" positions, such as angling, from long axis A or short axis B may be used. In one embodiment, antenna 226 may be disposed along the perimeter of device 40. For example, antenna 226 may be placed against or on the shell or housing, or incorporated within the shell or housing 205, for example, as is discussed below. FIG. 3 shows an antenna 327, according to one embodiment of the invention, of a horizontal air coil, which is oriented such that loop(s) or coil(s) of antenna 327 may circle along short axis B of device 40, according to some embodiments of the present invention. According to one embodiment of the present invention, a plane or planes formed by the loop(s) or coil(s) may be perpendicular to a supporting board 304 (e.g. a PCB), and may be in parallel with long axis A.

In another embodiment, for example when using a spherically shaped in-vivo device, the antenna may form a coil or set of coils lying in a plane or planes that are parallel to a circuit board or support on which the antenna is mounted, rather than forming a coil or set of coils in a plane or planes perpendicular to the support or circuit board. Further, in an embodiment including a spherically shaped device, the antenna may be disposed around the perimeter of the device, for example around the inside of a shell or housing of the device. Other dimensions and shapes for the antenna and for the in-vivo device, and other number of turns of coil may be used.

According to one embodiment of the present invention, a cumulative height or length (depending on the perspective) "H" of a series of stacked coils or loops, as is depicted by antenna 226 in FIG. 2, may be less than the diameter "D" of the stacked coils or loops. The set of loops or coils (when used herein the term "set" may include one unit or more than one unit) may extend along the length H. According to another embodiment of the present invention, diameter D of two or more loops or coils of antenna 226 may be slightly different from each other. For example, one coil may be slightly smaller than, and therefore may be contained within, another coil when antenna 226 is imprinted on a PCB, or other supporting medium and so different coils may be formed in substantially the same plane.

Figure 4A:
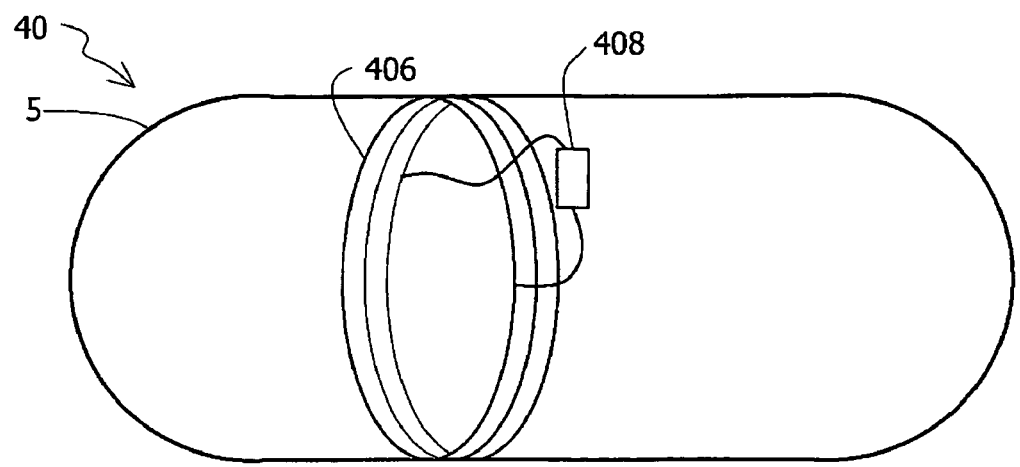
FIGS. 4A-4C are schematic illustrations of vertical antennas imprinted on a housing of an in-vivo device, in accordance with some embodiments of the present invention.

FIG. 4A is a simplified schematic illustration of a vertical antenna 406 imprinted on a shell or housing 5 of an in-vivo device 40, in accordance with some embodiments of the present invention. The imprint of antenna 406 may be, for example, on the inner side or the outer side of the shell or housing 5, and preferably on the inner side. When the imprint of antenna 406 is on the outer side of the shell or housing 5, care should be exercised to ensure that proper electrical connection of antenna 406 to a transmitter 408 is made through, for example, piercing a pin-size hole on the housing wall and subsequently sealing the hole so that fluid, which may come from the inside of a patient's GI or lumen, may not enter the compartment of device 40. According to some embodiments of the present invention, antenna 406 may be placed on a perimeter surrounding a long axis of device 40 but need not be. Further, device 40 need not have one axis longer than the other e.g., it may be symmetrical, spherical, etc.

According to some embodiments of the present invention, the in-vivo device 40 may include a shell or housing, which may be one piece but may also be multiple pieces, such as for example a main body piece and an optical dome piece. Typically, the shell or housing is formed from suitable plastic, but may also be made of other materials, such as glass, metal, etc. According to some embodiments of the present invention, an antenna, or a portion of the antenna, or a majority of the antenna, may be placed generally around an inside perimeter of the shell. Preferably, the antenna is disposed around the longest internal perimeter, to increase loop or coil area, but need not be.

Figure 4B:
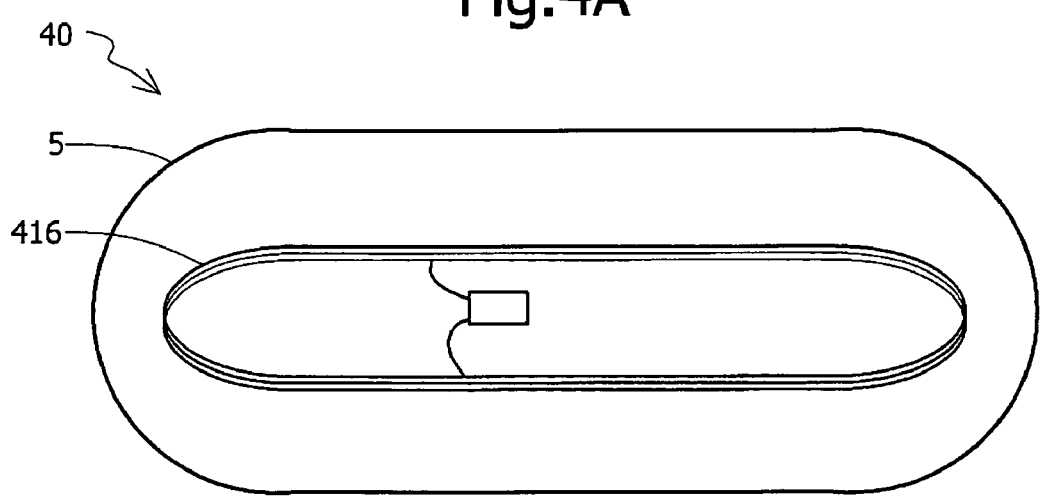

According to some embodiments of the present invention as shown in FIG. 4B, an in-vivo device 40 may include an antenna 416 which is imprinted on a shell or housing 5, either on the inner or outer side of the in-vivo device 40. In order to form maximum achievable coil area, antenna 416 may lie in a plane that is parallel to, or goes through a long axis of device 40.

Figure 4C:
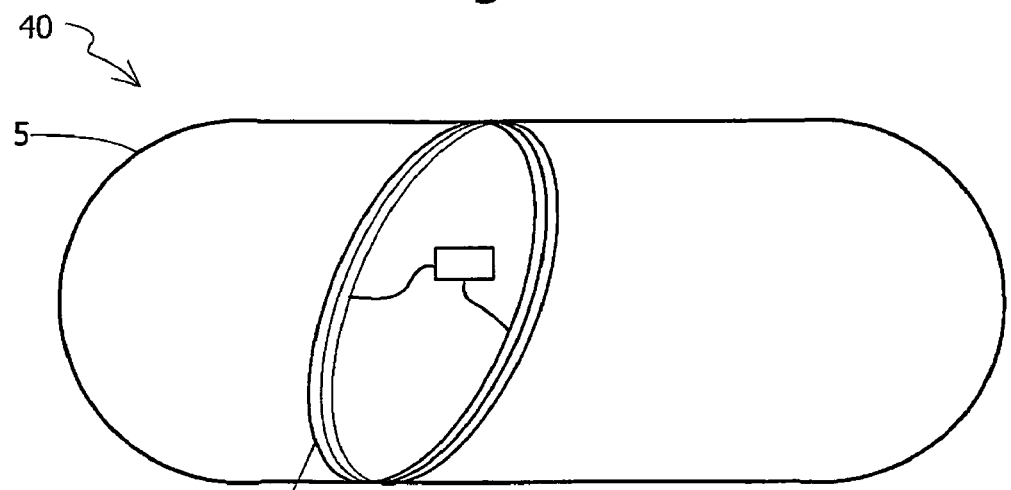

According to some embodiments of the present invention as shown in FIG. 4C an antenna 426 may be imprinted on the housing 5 of an in-vivo device 40, in a non-straight angle relative to the long axis of the housing of device 40. A vertical antenna 426 may have less coil area than in an antenna of 416, but more than in an antenna of 406.

Figure 5:
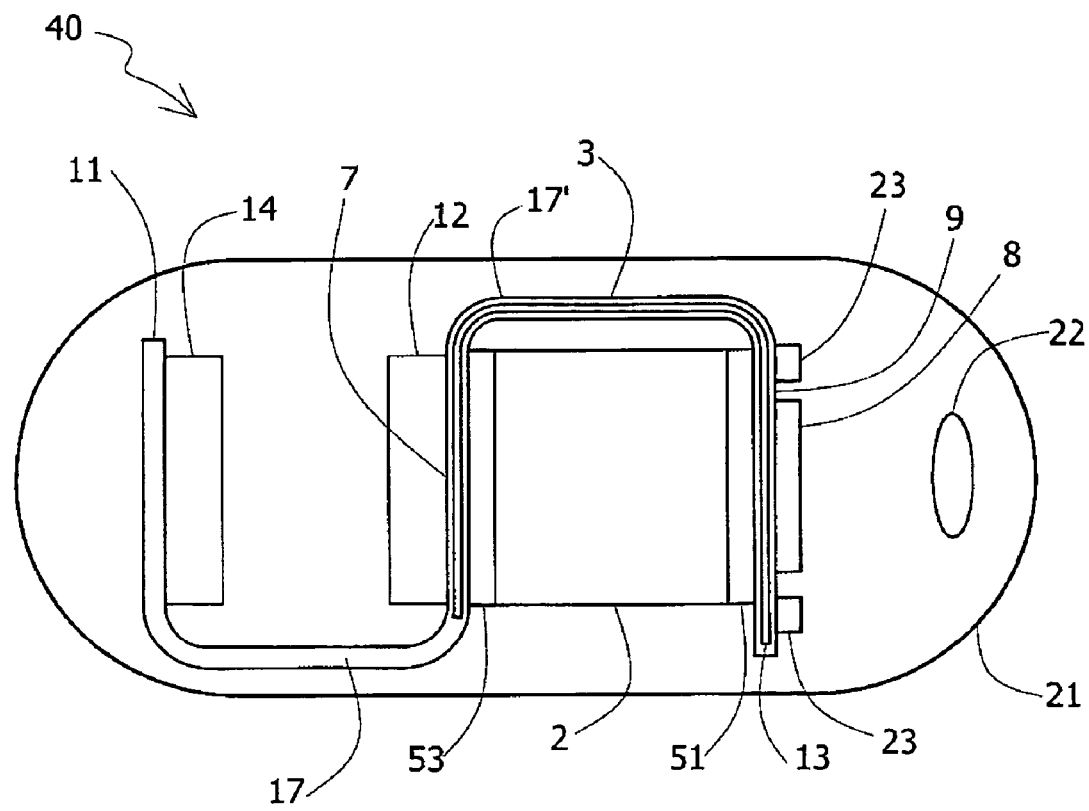
FIG. 5 is a schematic diagram of an in vivo imaging device, in accordance with some embodiments of the present invention.

FIG. 5 schematically illustrates an in vivo imaging device according to another embodiment of the present invention. According to one embodiment the device 40 may include an optical window 21 and an imaging system for obtaining images from inside a body lumen, such as the GI tract. According to one embodiment of the present invention, the imaging system may include an illumination system which may include for example, one or more illumination sources 23, such as a white LED, an OLED, an illumination ring or an illumination assembly, a hybrid illumination unit or other suitable illumination units. According to one embodiment of the present invention, the imaging system may include an image sensor for example an imager 8, such as a CMOS imaging camera and an optical system 22 which focuses the images onto the imager 8. According to one embodiment of the present invention, the illumination sources 23 may illuminate the inner portions of the body lumen through optical window 21. According to some embodiments of the present invention, device 40 may include a control unit 14, a transmitter/receiver 12 and an antenna 13 for transmitting and/or receiving signals such as image signals from the imager 8, and a power source 2, such as a silver oxide battery, that provides power to the electrical elements of the device 40.

Optionally, according to one embodiment of the present invention, transmitter 12 may include a processing unit or processor or controller, for example, to process signals and/or data generated by imager 8. In another embodiment, the processing unit may be implemented using a separate component within device 40, e.g., controller or processor 14, or may be implemented as an integral part of imager 8, transmitter/receiver 12, or another component, or may not be needed. The optional processing unit may include, for example, a Central Processing Unit (CPU), a Digital Signal Processor (DSP), a microprocessor, a controller, a chip, a microchip, a controller, circuitry, an Integrated Circuit (IC), an Application-Specific Integrated Circuit (ASIC), a Field Programmable Gate Array (FPGA) or any other suitable multi-purpose or specific processor, controller, circuitry or circuit. In one embodiment, for example, the processing unit or controller may be embedded in or integrated with transmitter/receiver 12, and may be implemented, for example, using an ASIC.

According to one embodiment of the present invention, the various components of the device 40 may be disposed on a support, for example a flexible circuit board and/or a circuit board 3 including rigid and flexible portions; preferably the components are arranged in a stacked vertical fashion, however, other arrangements are possible. For example, according to one embodiment of the present invention, one rigid portion 11 of the circuit board 3 may hold a control unit 14. Another rigid portion 9 of the circuit board may include, for example, an illumination system, such as one or more illumination sources 23 such as LEDs, OLEDs, a LED ring or other illumination source, and an imager 8 on one side; the other side of this rigid portion 9 may include, for example, a contact 51 for battery or power source 2. According to one embodiment the battery contact is preferably a spring, such as described below. Another rigid portion 7 of the circuit board 3 may include, for example, another battery contact 53 on one side; the other side of this rigid portion 7 may include, for example a transmitter/receiver 12. According to some embodiments of the present invention, each rigid portion of the circuit board may be connected to another rigid portion of the circuit board by a flexible connector portion (e.g. 17 and 17') of the circuit board.

Figure 6A:
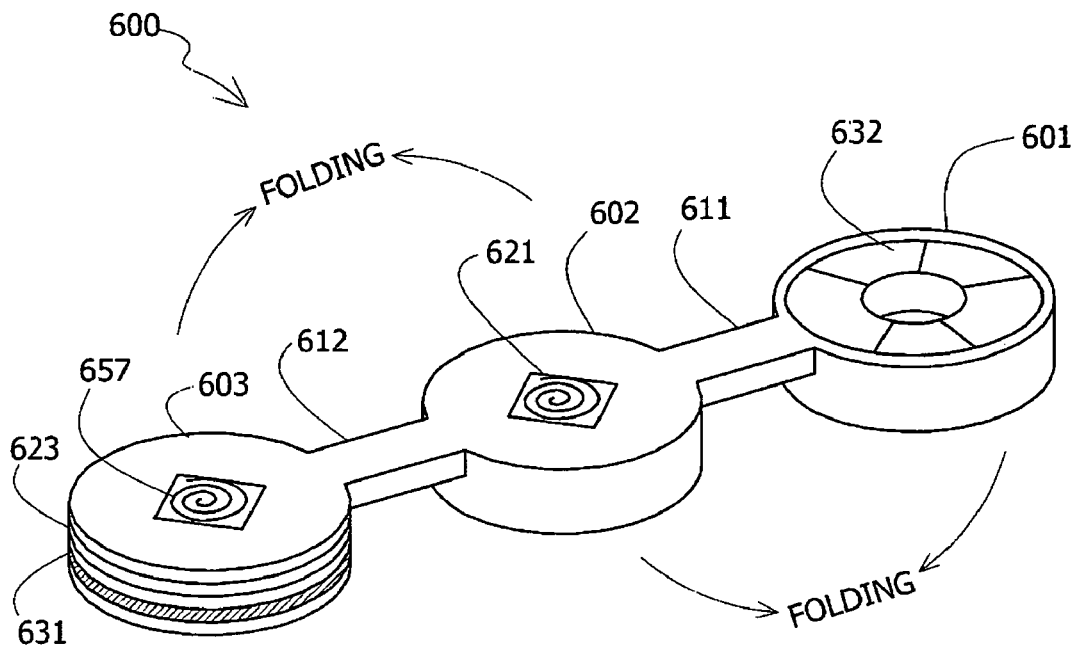
FIGS. 6A and 6B schematically illustrate a top side view and a bottom side view, respectively, of a circuit board in accordance with another embodiment of the present invention.
Figure 6B:
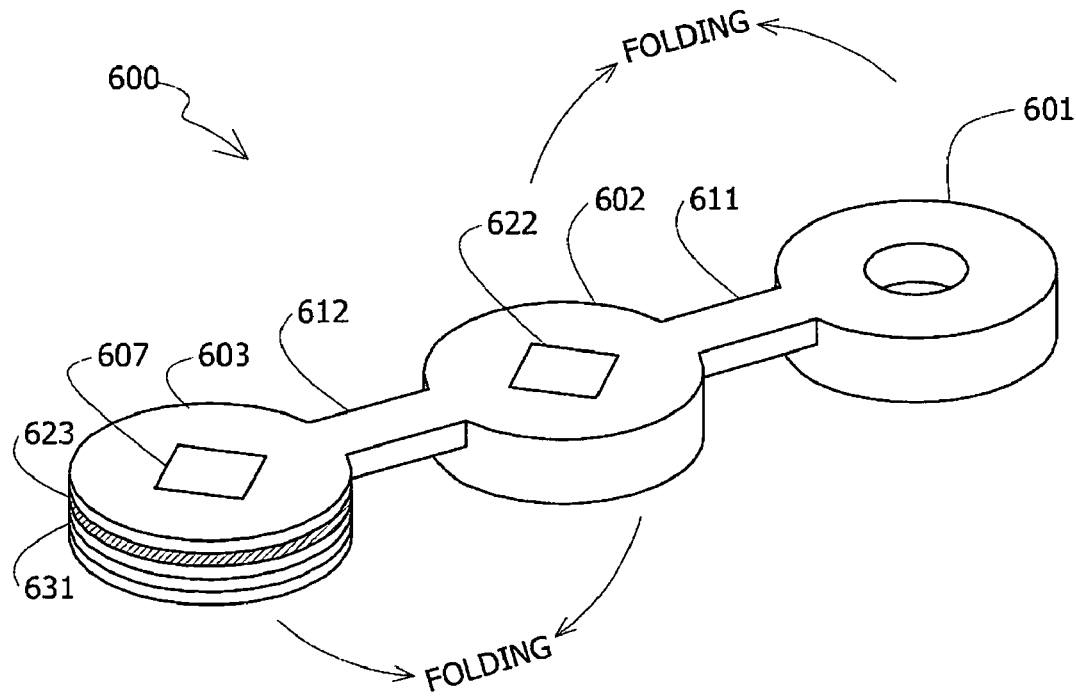

According to one embodiment of the present invention, the circuit board 3 may be folded, for example, as shown in FIGS. 5, 6A and 6B. When folded, the battery contacts may contact a set of one or more batteries, e.g., power source 2, which may be sandwiched between two rigid circuit board portions. The circuit board 3 may be folded in various manners, for example, circuit board 3 may have a "2" shape, a "5" shape, a "6" shape, a "C" shape, or other suitable shapes. FIG. 5 schematically shows according to one embodiment of the present invention, a circuit board, arranged as an "S" with rigid portions 9, 17 and 11 and alternating flexible portions 17 and 17'.

In alternate embodiments, a circuit board having rigid portions and flexible portions may be used to arrange and hold components in other in vivo imaging devices, such as a swallowable capsule measuring pH, temperature or pressure, or in a swallowable imaging capsule having components other than those described above. Such circuit boards may be similar to embodiments described in U.S. application Ser. No. 10/879,054 entitled IN VIVO DEVICE WITH FLEXIBLE CIRCUIT BOARD AND METHOD FOR ASSEMBLY THEREOF, and U.S. application No. 60/298,387 entitled IN VIVO IMAGING DEVICE WITH A CIRCUIT BOARD HAVING RIGID SECTIONS AND FLEXIBLE SECTIONS, each incorporated by reference herein in their entirety.

As mentioned above, as long as an antenna is significantly smaller than its transmission wave length, the reception and broadcast efficiency of the antenna will increase in direct relation to the surface area and/or the length of the antenna e.g. the longer the antenna and/or the bigger the surface area of the antenna, the more efficient it is. According to some embodiments of the present invention, an antenna 13, which is for example longer than the in-vivo device 40 may be inserted into an in-vivo imaging device, such as device 40, by attaching/embedding an antenna such as antenna 13 to circuit board 3, or to a layer within circuit board 3. For example according to one embodiment of the present invention an antenna 13 may be attached to rigid portion 9 and/or 7 and/or flexible portion 17', or may be integrated or embedded within a layer of rigid portion 9 and/or 7 and/or flexible portion 17'. For example, according to one embodiment of the present invention rigid portions 9 and 7 and/or flexible portion 17' of circuit board 3 may be manufactured such that antenna 13 is an integral part of circuit board 3.

According to some embodiments of the present invention, antenna 13 may be formed, manufactured or produced as an integrated or integral part of circuit board 3 or rigid portion 9. For example, a process of manufacturing circuit board 3 or rigid portion 9 may include bonding, gluing, soldering, connecting, or otherwise firmly attaching antenna 13 as a part of circuit board 3. Such manufacturing may result in a pre-provided circuit board 3 or rigid portion 9 having an antenna 13 integrated therein, and may eliminate the need to assemble or further connect antenna 13 to circuit board 3 or rigid portion 9 after the manufacturing process of circuit board 3 or rigid portion 9 is completed.

According to some embodiments of the present invention in order to form maximum achievable coil area, antenna 13 may lie in a plane that is parallel to, or goes through the circuit board 3. In addition, the loops of vertical antenna 13 may be imprinted close to the perimeter of circuit board 3 in order to form as much loop area as possible, and thereby increase the efficiency of antenna 13.

According to some embodiments of the present invention, when imprinted in or on the circuit board 3, loops of antenna 13 may be made to have slightly different diameters from each other. For example, one loop may be slightly smaller than, and therefore be contained within, another loop so that different loops may be made in a single layer of the circuit board 3. In addition, loops of antenna 13 may be made on different layers of the circuit board 3 with substantially same diameters.

FIGS. 6A and 6B schematically illustrate a top side view and a bottom side view, respectively, of a circuit board or other suitable substrate or support 600, configured to occupy a minimum of space within device 40 and include a foldable antenna, in accordance with some embodiments of the present invention.

According to one embodiment of the present invention, circuit board 600 may include rigid portions 601, 602 and 603, which may be interconnected using flexible portions 611 and 612. Although three rigid portions and two flexible portions are shown, embodiments of the present invention are not limited in this regard, and may include other numbers, orders or combinations of rigid portions and/or flexible portions. According to some embodiments of the present invention, rigid portion 601 may include, for example, an illumination system 632 e.g. a hybrid illumination unit and/or an illumination ring such as a LED ring or an OLED ring. According to some embodiments of the present invention, rigid portion 602 may include an imager 622 on one side; the other side of this rigid portion 602 may include, for example a battery holder 621, e.g., a spring able to hold a battery or other power source in place. According to some embodiments of the present invention, rigid portion 603 may include a transmitter such as an ASIC 607 and a battery holder 651.

According to some embodiments of the present invention, each rigid portion may be equal to or less than 8 mm in thickness. According to one embodiment of the present invention the circuit board 600 may include one or more layers, wherein an antenna, for example the antenna 623 may be embedded in one of the layers or partially in all of the layers e.g. an antenna having a spiral shape with a dimension of depth. For example rigid section 603 may include six layers 631, wherein the antenna 623 may be embedded in one, several or in all of the layers. According to one embodiment of the present invention, one of the layers may include an electrical connection which may connect the antenna 623 to, for example ASIC 607 located for example in rigid section 603.

According to one embodiment of the present invention, the layers of the circuit board may include any sort of known material; according to some embodiments copper is used.

Figure 6C:
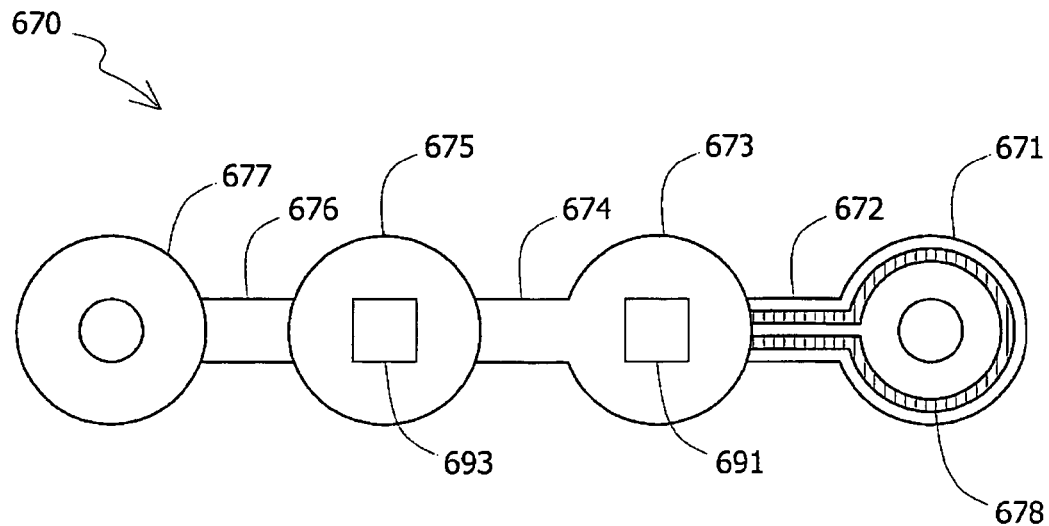
FIGS. 6C and 6D schematically illustrate a top view and a bottom view, respectively, of a circuit board in accordance with some embodiments of the present invention.
Figure 6D:
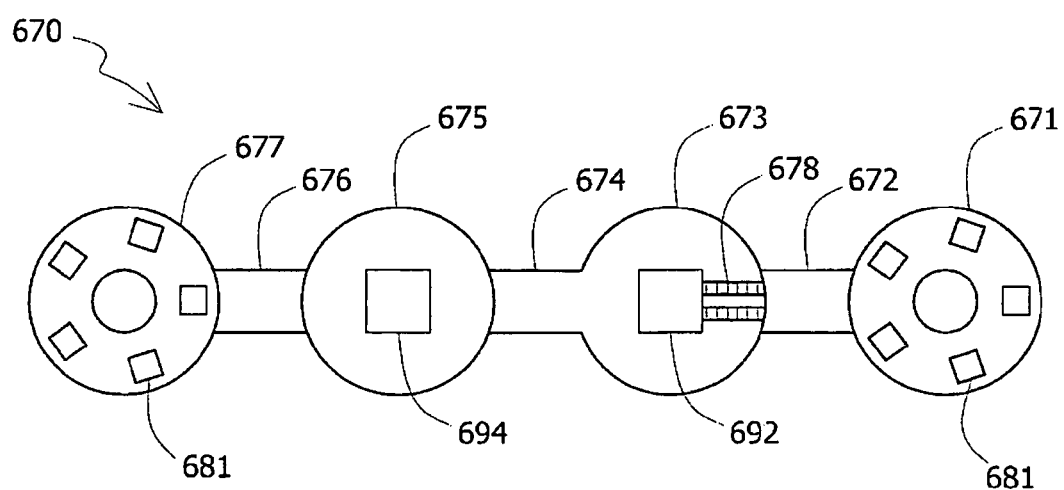

FIGS. 6C and 6D schematically illustrate a top view and a bottom view, respectively, of a circuit board 670 in accordance with some embodiments of the present invention. In some embodiments, circuit board 670 may be used in conjunction with device 40 of FIG. 5, or with other suitable devices and systems for in vivo imaging or in vivo sensing.

According to one embodiment of the present invention circuit board 670 may include, for example, one or more rigid portions and one or more flexible portions. For example, circuit board 670 may include rigid portions 671, 673, 675 and 677, which may be interconnected using flexible portions 672, 674 and 676. Although four rigid portions and three flexible portions are shown, embodiments of the present invention are not limited in this regard, and may include other numbers, orders or combinations of rigid portions and/or flexible portions.

In some embodiments, rigid portions 671 and 677 may include, for example, one or more illumination units such as LEDs 681, and optionally one or more resistors and/or capacitors, for example, to regulate or control the power provided to the LEDs 681.

In some embodiments, rigid portion 673 may include a first imager 691 and a transmitter such as an ASIC 692. According to some embodiments of the present invention, rigid portion 675 may optionally include a second imager 693 and/or a processor 694. According to some embodiments of the present invention, an antenna such as a circular loop antenna 678, may be mounted on and/or may be embedded in one or more sections of the circuit board 670. For example, according to one embodiment of the present invention, one part of the antenna 678 may be mounted on rigid portion 671, another part of antenna 678 may be mounted on flexible portion 672, and another part may be mounted on rigid portion and may be connected to ASIC 692.

Figure 7A:
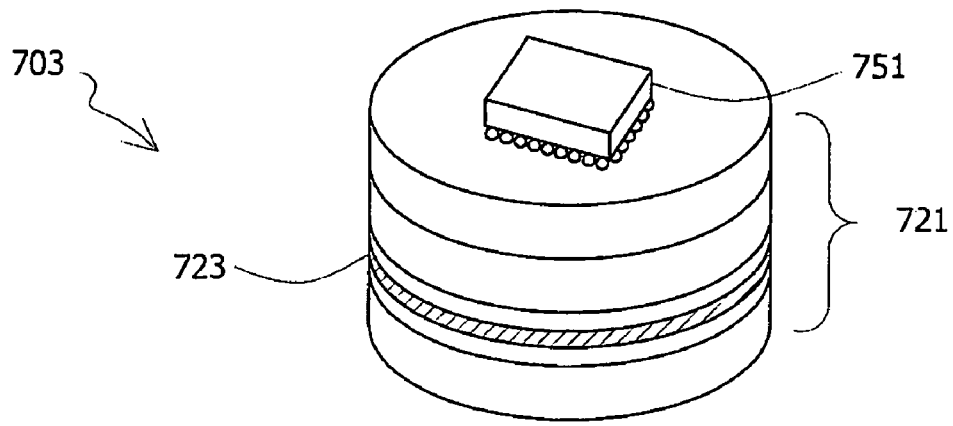
FIG. 7A is a cutaway view depicting a rigid portion of a circuit board, an antenna and a transmitter, according to some embodiments of the present invention.

FIG. 7A is a cutaway view depicting a rigid portion 703 an antenna 723 and a transmitter 751, according to some embodiments of the present invention. In some embodiments, rigid portion 703 may be an example of rigid portion 670 of FIGS. 6A and 6B. According to some embodiments of the present invention the rigid portion 703 may include one or more layers 721, for example six inner layers. Antenna 723 may be embedded and/or printed in one of the layers, and may be electrically interconnected, for example to the transmitter 751. According to one embodiment of the present invention, antenna 723 may be coiled on the inside of rigid portion 703, for example in one of the layers. According to one embodiment of the present invention, rigid portion 703 may have a cylindrical shape, and antenna 723 may be wrapped around the outside of rigid portion 703.

Figure 7B:
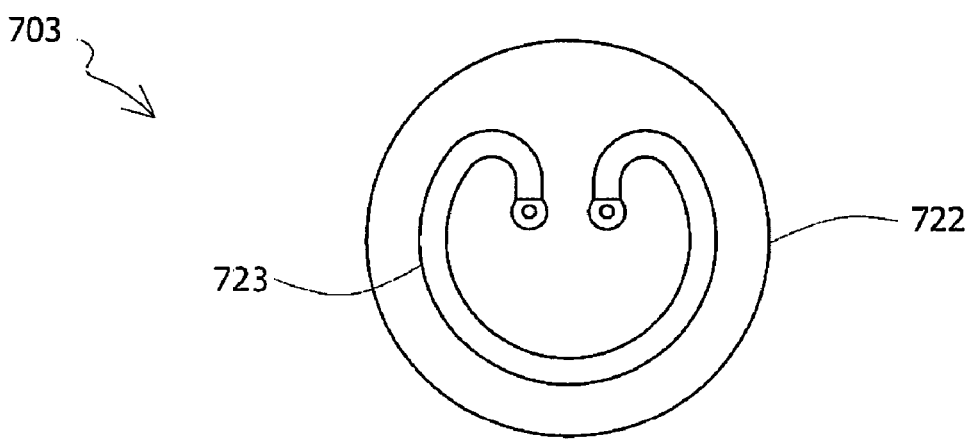
FIGS. 7B-7C schematically illustrate a top view and a side view, respectively, of a rigid section of a circuit board, in accordance with some embodiments of the present invention.
Figure 7C:
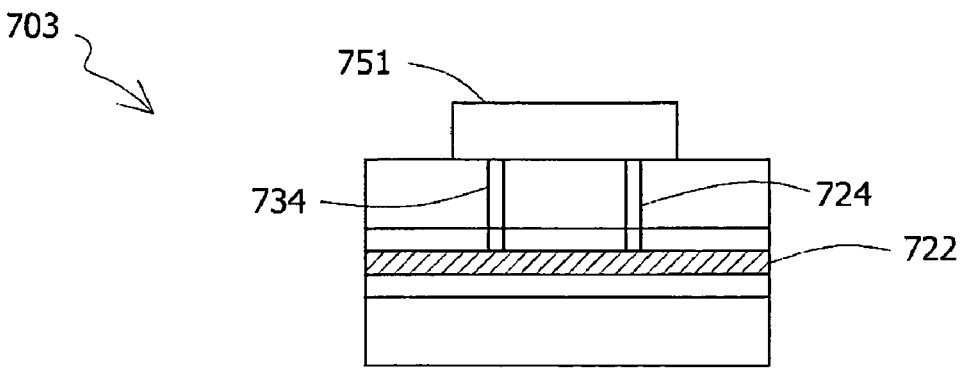

FIGS. 7B-7C schematically illustrate a top view and a side view, respectively, of an inner layer, for example of rigid section 703, in accordance with some embodiments of the present invention, According to some embodiments of the present invention, antenna 723 may communicate electrically, for example, through vias and/or wires and/or electrical contacts that may cross from one side of rigid section 703 to the other through one of the layers. According to one embodiment of the invention electrical wires, for example two printed traces 724 and 734, may be printed and/or molded on one of the layers 721. According to one embodiment of the present invention, each of the printed traces 724 and 734 may be connected either to a transmitter 751, or to other components which may be placed for example on circuit board 603.

Figure 8A:
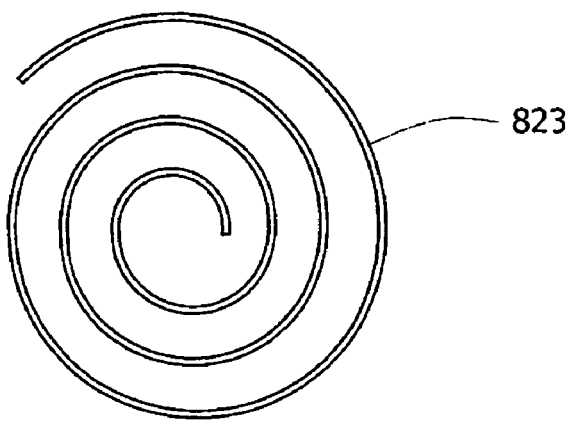
FIGS. 8A-8D schematically illustrate an antenna, according to some embodiments of the present invention.
Figure 8B:
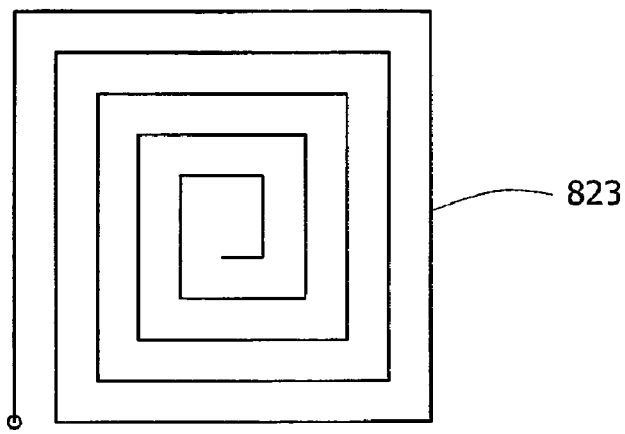
Figure 8C:
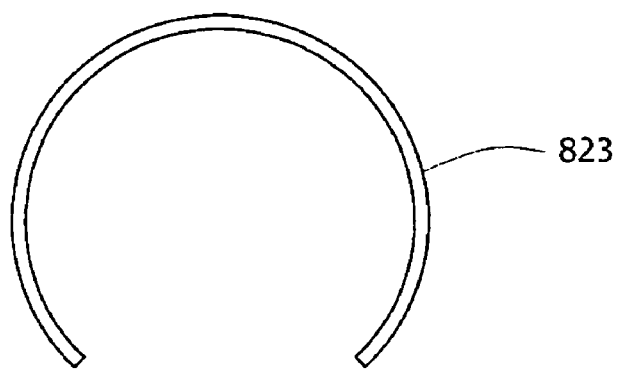

Reference is now made to FIGS. 8A-8C, which are schematic diagrams illustrating an antenna 823, according to some embodiments of the present invention. According to one embodiment, for example as shown in FIG. 8A, the antenna 823 may be a circular spiral shaped. According to one embodiment of the present invention, for example as shown in FIG. 8B, the antenna 823 may be a square spiral shaped antenna. According to another embodiment of the present invention, for example as shown in FIG. 8C, the antenna may be a ring or a boomerang shaped, for example with an internal circle e.g. a rounded hole in its center. Typically, the antenna 823 has compatible measurements for a suitable incorporation into a circuit board, for example into one of the layers in the rigid portion 703. The antenna 823 may be of a different shape other than a ring shape e.g. a rectangular, or of any other form compatible for fitting into an in vivo device, e.g., an ingestible capsule.

Figure 8D:
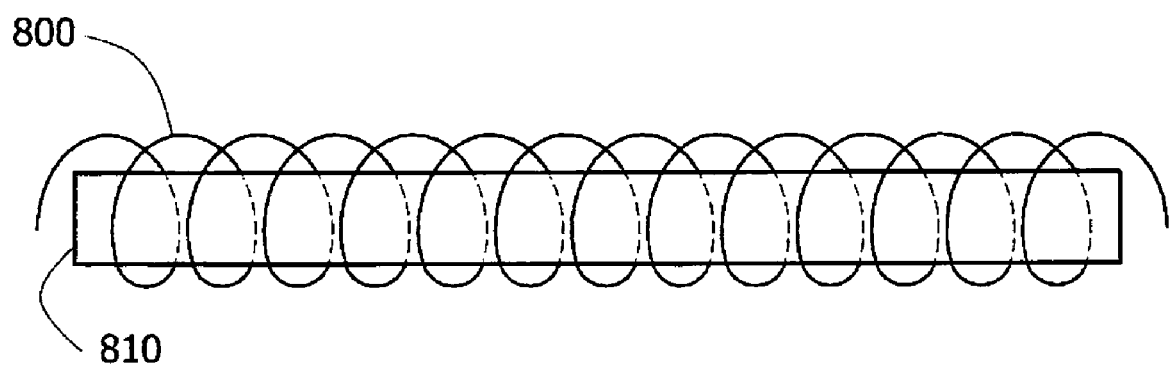

FIG. 8D depicts an antenna 800, such as a horizontal air coiled antenna, according to some embodiments of the present invention. The efficiency of, for example the antenna 800 may be improved by using one or more components for example a flexible stick 810 containing ferrite. For example, in low frequencies such as 10 MHz the fortitude of the field surrounding an antenna, such as antenna 800 may be intensified a hundred fold, by placing stick 810 within the coiled antenna 800 for example along the hollowed coil of the coiled antenna 800.

Figure 9A:
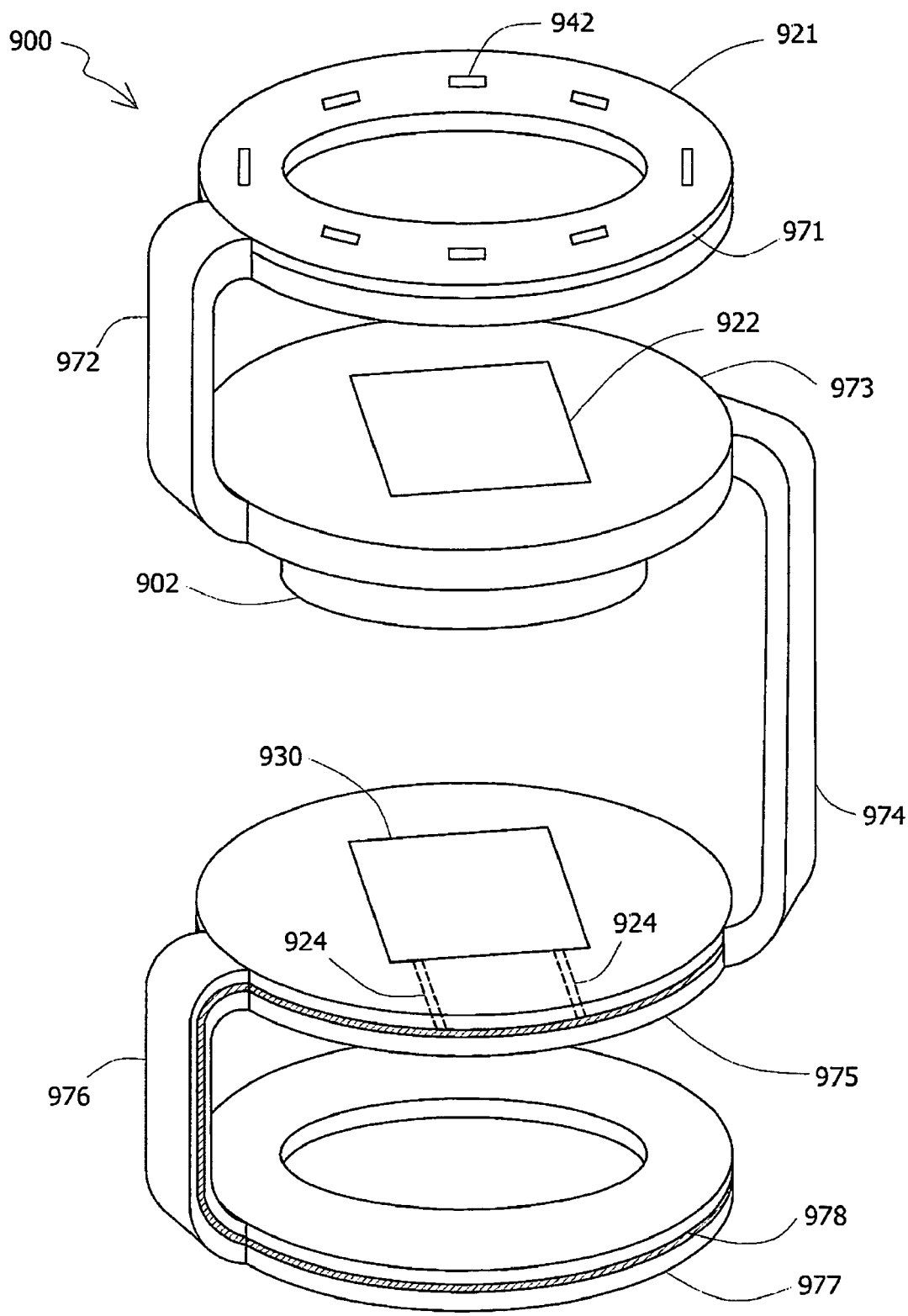
FIG. 9A schematically illustrates a three-dimensional view of a circuit board and an antenna, in accordance with some embodiments of the present invention.

FIG. 9A schematically illustrates a three-dimensional view of a circuit board 900 in accordance with some embodiments of the present invention. According to some embodiments of the present invention, circuit board 900 may be an example of circuit board 600 of FIGS. 6A and 6B. In some embodiments, circuit board 900 may be used in conjunction with device 40 of FIG. 5 or with other suitable devices and systems for in vivo imaging.

According to one embodiment of the present invention circuit board 900 may include, for example, one or more rigid portions and one or more flexible portions. For example, circuit board 900 may include rigid portions 971, 973, 975 and 977, which may be interconnected using flexible portions 972, 974 and 976. Although four rigid portions and three flexible portions are shown, embodiments of the invention are not limited in this regard, and may include other numbers, orders or combinations of rigid portions and/or flexible portions.

According to one embodiment of the present invention, rigid portion 971 may have mounted on it on one face a lens holder and a LEDs ring 921 having one or more illumination units or LEDs 942, and possibly other components. According to some embodiments of the present invention, rigid portion 973 may include an imager 922 on one side; the other side of this rigid portion 973 may include, for example a battery holder 902.

According to some embodiments of the present invention the circuit board 900 may optionally include one or more layers and an antenna may be embedded in one of the layers. For example according to one embodiment of the present invention an antenna 978 may be embedded in one of the layers of the rigid sections 975 and 977 and the flexible section 976 of circuit board 900. According to some embodiments of the present invention, the antenna 978 may be connected to a transmitter, such as transmitter 930 which is located at rigid portion 975. The various components, for example transmitter 930 may communicate electrically, for example, through vias 924 and/or wires and/or electrical contacts embedded in the circuit board 900.

Figure 9B:
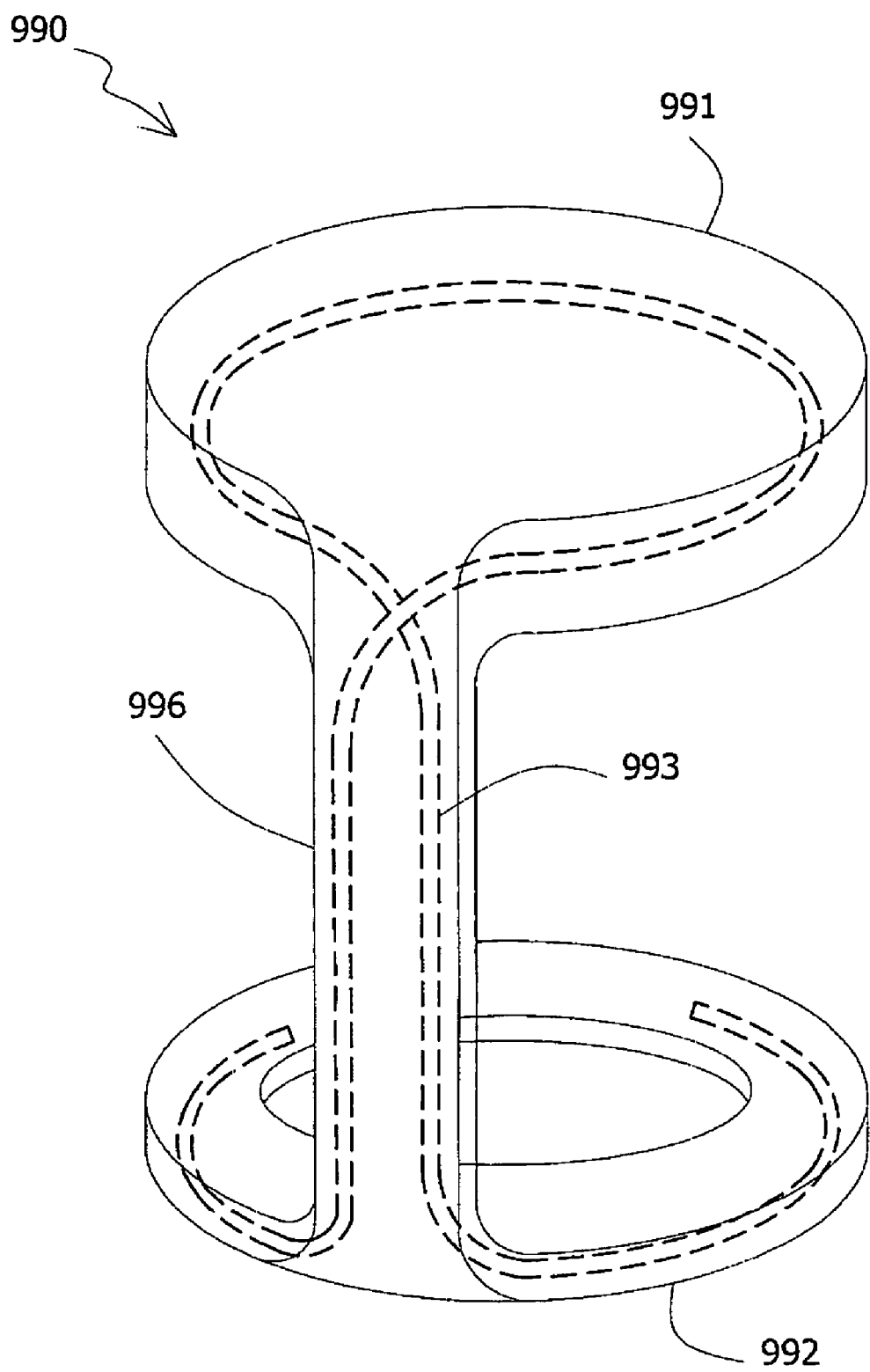
FIGS. 9B and 9C schematically illustrate a three-dimensional (3D) view and a top view, respectively, of a 3D circuit board and a 3D antenna in accordance with some embodiments of the present invention.
Figure 9C:
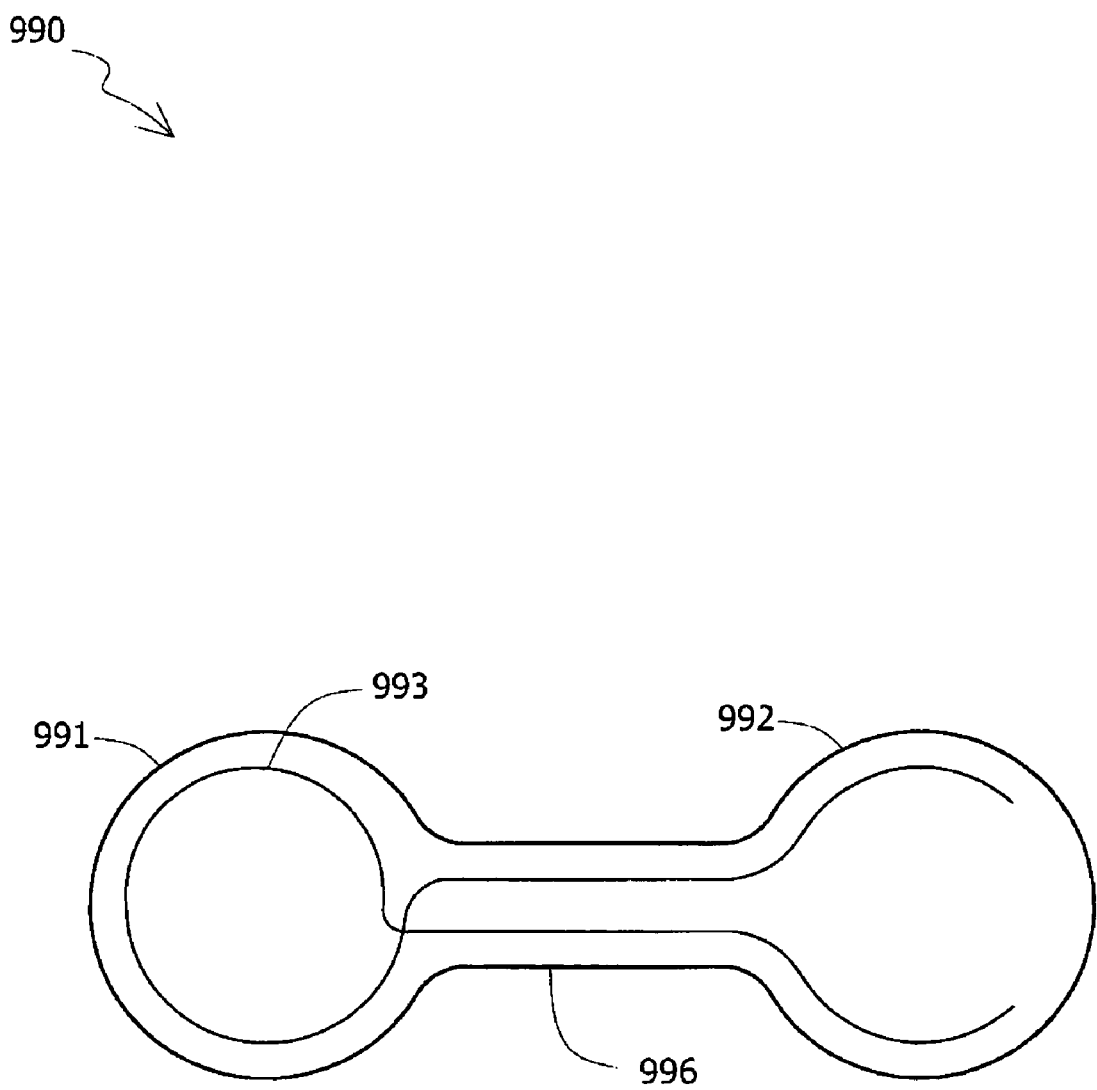

FIGS. 9B and 9C schematically illustrate a three-dimensional (3D) view and a top view, respectively, of a 3D circuit board 990 and a folded antenna 993 e.g. a 3D antenna, in accordance with some embodiments of the present invention. In some embodiments, circuit board 990 may be used in conjunction with device 40 of FIG. 5 or with other suitable devices and systems for in vivo imaging or in vivo sensing.

According to one embodiment of the present invention circuit board 990 may include, for example, one or more rigid portions and one or more flexible portions. For example, circuit board 990 may include rigid portions 991 and 992, which may be interconnected using a flexible portion 996. Although two rigid portions and one flexible portion are shown, embodiments of the invention are not limited in this regard, and may include other numbers, orders or combinations of rigid portions and/or flexible portions.

According to some embodiments of the present invention the circuit board 990 may optionally include one or more layers and an antenna 993 may be embedded in one or more of the layers. According to some embodiments of the present invention the antenna 993 may be used inside device 40 by placing or embedding the antenna 993 alongside the circuit board 990 and folding the circuit board within device 40. According to some embodiments of the present invention the antenna 993 may surround the circuit board 970.

Figure 9D:
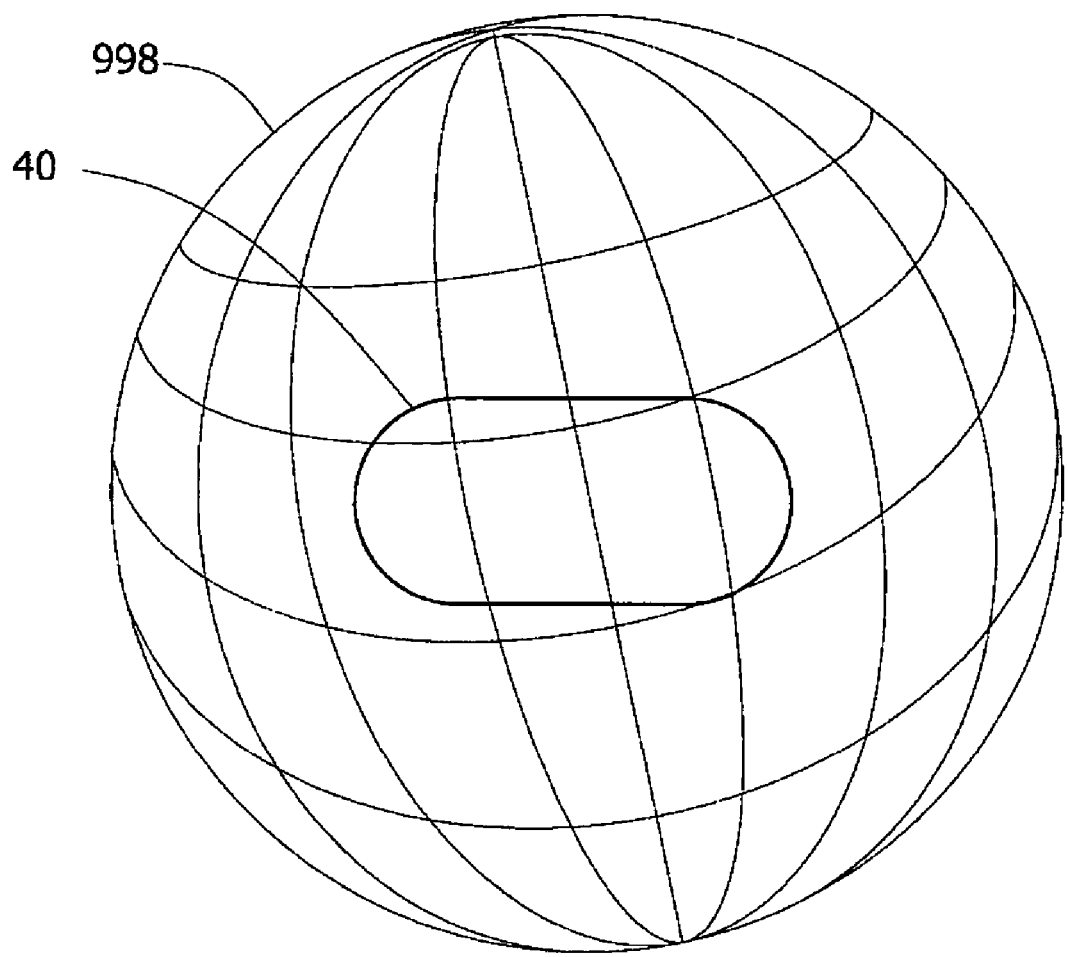
FIG. 9D illustrates a diversity polarization field of a 3D antenna, in accordance with some embodiments of the present invention.

According to some embodiments of the present invention, as shown in FIG. 9D, by folding an antenna such as antenna 993, for example within circuit board 990 or within device 40, or with other suitable devices and systems, an antenna which includes conductors in three dimensions is formed wherein each conductor radiates in a different direction. As a result a uniform field such as a diversity polarization field 998 is generated around the antenna and/or around device 40.

Figure 9E:
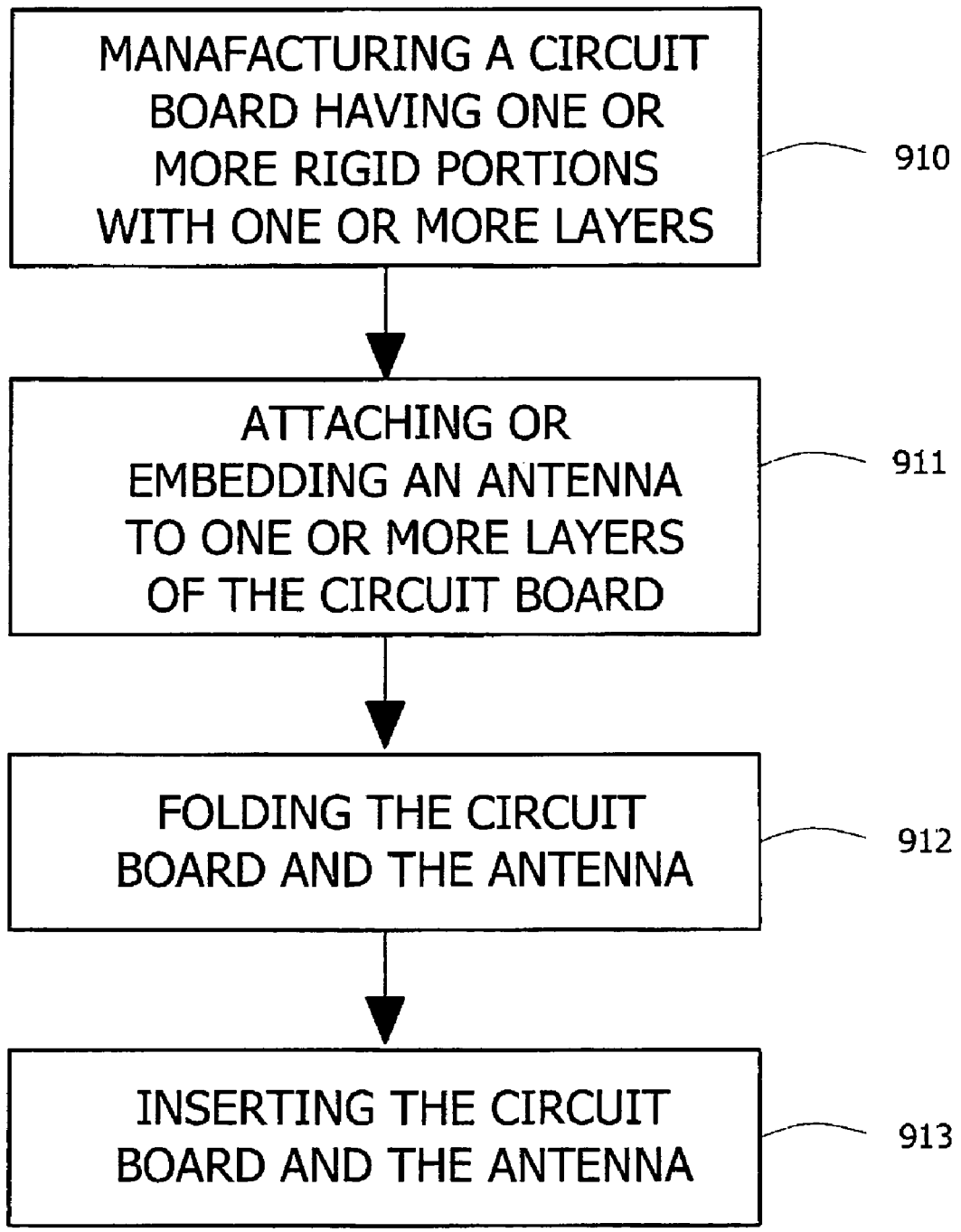
FIG. 9E is a schematic flow-chart of a method of manufacturing a 3D antenna, in accordance with some embodiments of the invention.

FIG. 9E is a schematic flow-chart of a method of manufacturing an in vivo imaging device with a foldable antenna, in accordance with some embodiments of the invention. In step 910 a circuit board having rigid portions and flexible portions with one or more layers is provided. In step 911 an antenna may be attached, connected or embedded to one or more of the layers of the circuit board. This may include, for example, attaching or embedding the antenna alongside the entire circuit board. In step 912 the circuit board e.g. and the antenna may be folded, bended, twisted and/or shaped, for example, into a pre-defined shape. In step 913, the circuit board and the antenna may be inserted into a suitable housing adapted or configured for in vivo imaging, for example, a housing of a swallowable capsule. A 3D antenna and a device including such an antenna may be produced according to embodiments of the invention. According to one embodiment an imager may be attached or embedded to the circuit board. Other suitable operations or methods may be used in accordance with embodiments of the invention.

Figure 10:
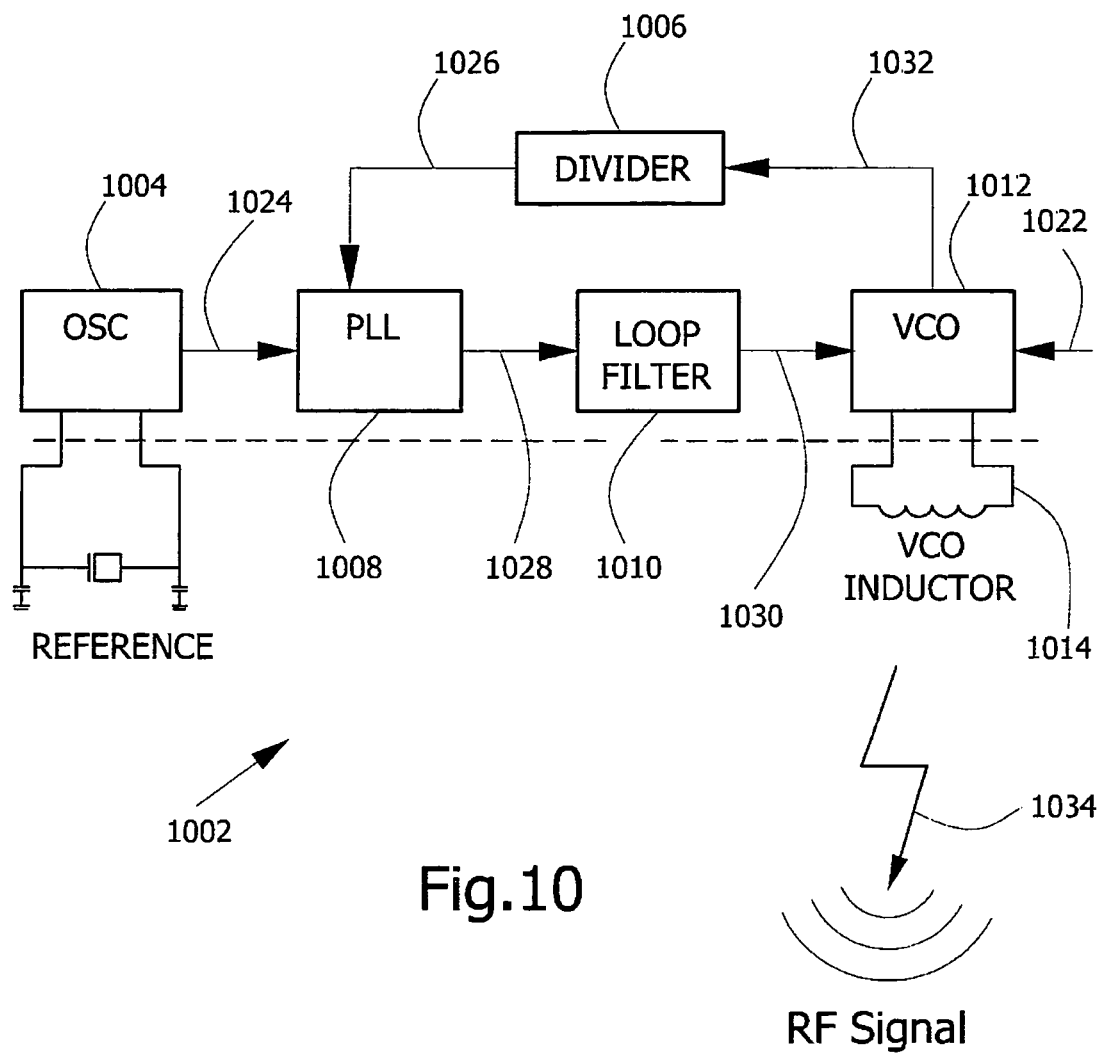
FIG. 10 is a block-diagram illustration of an exemplary transmitter containing a voltage-controlled oscillator, in accordance with some embodiments of the present invention.

FIG. 10 is a simplified block-diagram illustration of an exemplary transmitter 1002 containing a voltage-controlled oscillator (VCO) 1012 and using a resonating coil 1014 of VCO 1012 to function as an antenna, according to some embodiments of the present invention.

According to one embodiment of the present invention, a crystal oscillator (OSC) 1004 may provide a relatively stable and accurate reference frequency 1024. The reference frequency 1024 is then fed into a phase lock loop (PLL) 1008. A second input 1026 to the PLL may come from the output of a binary divider 1006, which may properly divide the frequency of an input signal 1032, tapped directly from the output of VCO 1012 for example, and output a signal whose frequency may be sufficiently close to the reference frequency 1024. The PLL 1008 may produce an output current signal 1028, which may be close to zero and may be proportional to the relative phase difference of its two input signals, 1024 and 1026. If the reference signal 1024 and the input signal 1026 from divider 1006 are at substantially the same frequency, the output of PLL 1008 may be a constant zero current. Any noise on this voltage may be smoothed out by a low-pass loop filter 1010, which then produces a control voltage output 1030. If the two input signals to the PLL 1008 are not identical in frequency, the control voltage output 1030 from the low-pass loop filter 1010 may fluctuate, which may then attempt to drive the VCO 1012 to the correct frequency. Other components or sets of components may be used in transmitter 1002.

According to some embodiments of the present invention, a modulation signal 1022, e.g., a signal from a processor may be a digital binary signal but need not be. According to one embodiment of the present invention, modulation signal 1022 may include image data collected by the imaging system, and may also include other telemetry data such as pH data, pressure data, battery voltage data and the like. The modulation signal 1022 may be superimposed onto the control voltage signal 1030 of the VCO 1012 to produce a modulated signal 1034. According to some embodiments of the present invention, the modulation may be conducted in a format of frequency modulation (FM), phase modulation (PM), frequency-shifted-key (FSK), phase-shifted-key (PSK), minimum shift keying (MSK), continuous phase frequency shift keying (CPFSK) or any other suitable formats.

According to some embodiments of the present invention, a power amplifier may be used to further boost the power of modulated signal 1034 before it is applied to an antenna. However, this may not be an efficient way to power an antenna that is used inside imaging an in-vivo device, e.g., a swallowable capsule, wherein available power sources may be limited. According to some exemplary embodiments of the present invention, resonating coil 1014 of VCO 1012 may be used to function as an antenna, and modulated signal 1034 may be radiated by resonating coil 1014 directly. Additionally, relatively large dynamic range of radiation power, for example, 20 dB, may be achieved by changing the driving current that flows through VCO 1012.

The efficiency of an antenna is in general determined by characteristics of the antenna among which are the surface area and/or the length of the antenna. For example, as long as an antenna is significantly smaller than the antenna's transmission wave length, the reception and transmission efficiency of the antenna increases in direct relation to the surface area and/or the length of the antenna e.g. the longer the antenna is and/or the bigger the surface area of the antenna is, the more efficient it is. In addition, the antenna's impedance increases in direct relation to the surface area and the number of coils of the antenna. As a result the impedance of the antenna is changed (usually increases) by increasing the efficiency of the antenna.

According to some embodiments of the present invention it may be possible to match an antenna impedance to a required value by using a Matching Component e.g. an additional capacitance and/or chock.

According to one embodiment of the present invention, the employment of a Matching Component may enable effective use of bigger and longer antennas (e.g. with high efficiency and a predetermined range of impedance) such as the antenna depicted in FIG. 5, and adjust the desired range of impedance of the antenna with a Matching Component. According to some embodiments of the present invention, as shown in FIGS. 11A-11D, it will be possible to use antenna(s) of different shapes and sizes in combination with different capsule components such as an ASIC etc.

Figure 11A:
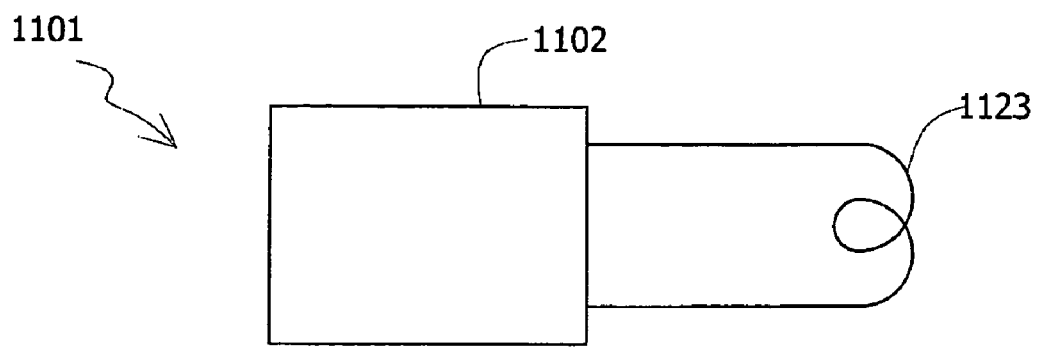
FIGS. 11A-11E are block-diagram illustrations of an electric circuit, in accordance with some embodiments of the present invention.

FIG. 11A schematically illustrates an electric circuit for example a resonant circuit such as a VCO (Voltage Controlled Oscillator) circuit 1101, in accordance with some embodiments of the present invention. According to one embodiment of the present invention, circuit 1101 may include a power amplifier 1102 or a power VCO and an antenna 1123. According to one embodiment of the present invention an inductive value of the antenna, for example antenna 1123 may be determined by the following equation:

$$f = \frac{1}{2} \pi \sqrt{LC}$$

Wherein:
f—frequency value of carrier wave,
L—Inductance value of the resonant circuit,
C—Capacitance value of the resonant circuit.

Figure 11B:
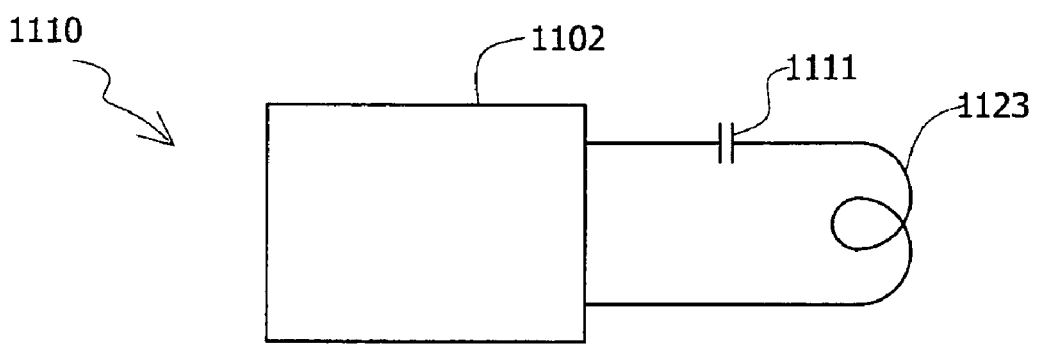

According to some embodiments of the present invention it may be possible to match an antenna inductance to a required value by using additional capacitance and/or chock. For example according to one embodiment, as shown in FIG. 11B, circuit 1110 may include a capacitance 1111, which may be connected in series to antenna 1123.

Figure 11C:
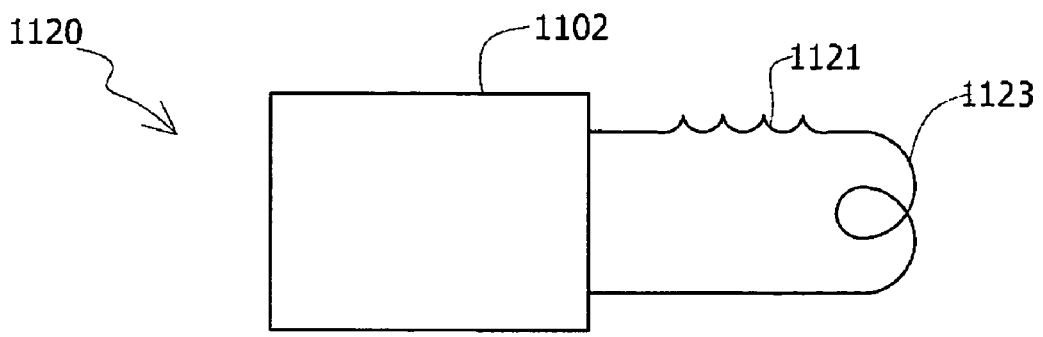

According to another embodiment of the present invention, as shown in FIG. 11C, circuit 1120 may include a chock 1121, which may be connected in series to antenna 1123.

Figure 11D:
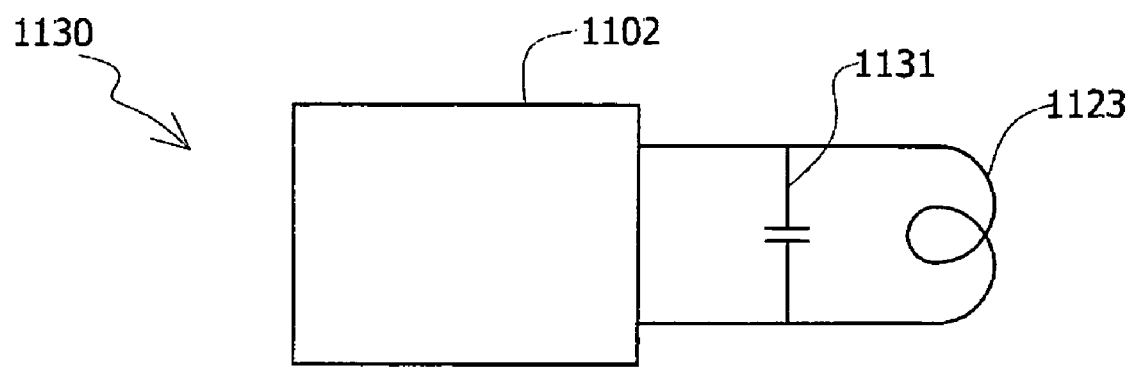

According to another embodiment of the present invention, as shown in FIG. 11D, circuit 1130 may include a capacitance 1131, which may be connected in parallel to antenna 1123.

Figure 11E:
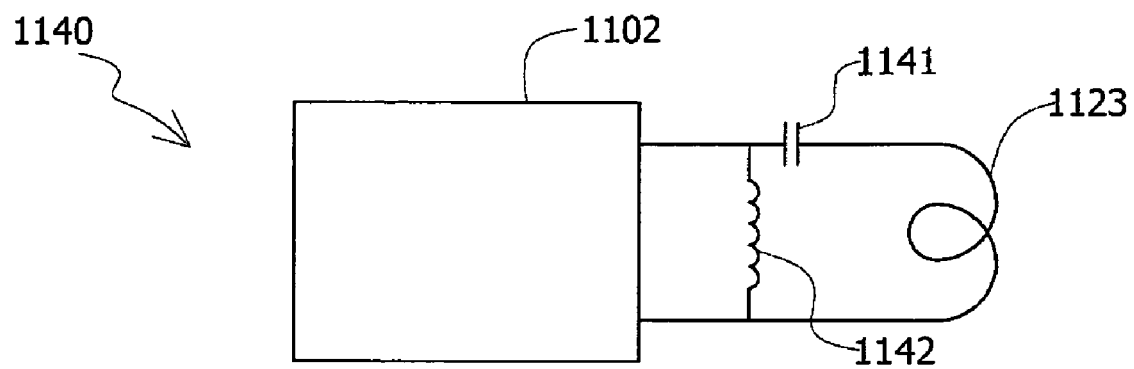

According to another embodiment of the present invention, as shown in FIG. 11E, circuit 1140 may include a chock 1142, which may be connected in parallel to capacitance 1141 and antenna 1123.

It will be appreciated by persons skilled in the art that the present invention is not limited to what has been particularly shown and described hereinabove. Rather, the scope of the present invention is defined by the claims which follow.

The invention claimed is:

1. An in vivo imaging device comprising:
    an antenna folded to form a three-dimensional antenna; and
    a support, said support comprising at least one flexible portion comprising at least one layer, said at least one flexible portion interconnecting two rigid portions having at least one layer;
    wherein said antenna is embedded within said at least one flexible portion of said support and within said two rigid portions of said support, and
    wherein a transmitter is disposed on one of said rigid portions.

2. The in vivo imaging device of claim 1, wherein said support is a circuit board.

3. The in vivo imaging device of claim 2, wherein an illumination system is mounted on said circuit board.

4. The in vivo imaging device of claim 1, wherein said transmitter is an ASIC.

5. The in vivo imaging device of claim 1, comprising an imager.

6. The in vivo imaging device of claim 1, wherein said in vivo imaging device is autonomous.

7. An autonomous in-vivo imaging device comprising:
    a housing;
    an antenna to form a three-dimensional antenna; and
    a circuit board, said circuit board comprising at least one flexible portion interconnecting two rigid portions;
    wherein said antenna is embedded within said at least one flexible portion of said circuit board and within said two rigid portions of said circuit board inside said housing, and
    wherein a transmitter is disposed on one of said rigid portions of said circuit board.

8. The in-vivo device according to claim 7, comprising an image sensor.

9. The autonomous in vivo imaging device of claim 7, comprising an imager.

10. A method of manufacturing an in-vivo device, the method comprising:
    embedding an antenna folded to form a three-dimensional antenna within two rigid portions of a circuit board and a flexible portion of said circuit board, the flexible portion interconnecting the two rigid portions, said circuit board comprising at least one layer;
    folding the circuit board into an in vivo imaging device housing; and
    disposing a transmitter on one of said rigid portions of said circuit board.

11. The method of claim 10, comprising mounting an imager on the circuit board.

* * * * *